United States Patent
Easter

(10) Patent No.: US 10,102,735 B2
(45) Date of Patent: Oct. 16, 2018

(54) SYSTEMS AND METHODS FOR HAND SANITIZATION MONITORING AND COMPLIANCE

(71) Applicant: Cullen Thomas Easter, Upland, CA (US)

(72) Inventor: Cullen Thomas Easter, Upland, CA (US)

(73) Assignee: Cullen Thomas Easter, Upland, CA (US)

(*) Notice: Subject to any disclaimer, the term of this patent is extended or adjusted under 35 U.S.C. 154(b) by 0 days.

(21) Appl. No.: 15/885,471

(22) Filed: Jan. 31, 2018

(65) Prior Publication Data

US 2018/0218591 A1 Aug. 2, 2018

Related U.S. Application Data

(60) Provisional application No. 62/452,851, filed on Jan. 31, 2017.

(51) Int. Cl.
*G08B 21/24* (2006.01)
*G16H 40/20* (2018.01)

(52) U.S. Cl.
CPC .......... *G08B 21/245* (2013.01); *G16H 40/20* (2018.01); *H04Q 2209/47* (2013.01)

(58) Field of Classification Search
CPC ........ C08G 61/02; C09D 165/00; G03G 5/07; G08B 21/245; G16H 40/20; H04Q 2209/47
USPC ...................................... 340/573.1
See application file for complete search history.

(56) References Cited

U.S. PATENT DOCUMENTS

| | | | | |
|---|---|---|---|---|
| 8,558,660 | B2* | 10/2013 | Nix | H04Q 9/00 340/10.1 |
| 9,000,930 | B2* | 4/2015 | Pelland | G01S 5/02 340/539.13 |
| 9,030,325 | B2* | 5/2015 | Taneff | G08B 21/245 340/573.1 |
| 9,143,843 | B2* | 9/2015 | De Luca | G08B 21/12 |
| 9,584,965 | B2* | 2/2017 | Good | H04W 4/02 |
| 2008/0099043 | A1* | 5/2008 | Barnhill | A46B 13/02 134/6 |
| 2008/0246599 | A1* | 10/2008 | Hufton | G01S 1/70 340/529 |
| 2009/0091458 | A1* | 4/2009 | Deutsch | G06Q 50/22 340/573.1 |

(Continued)

OTHER PUBLICATIONS

"Fundamentals of Vibration," University of Ferrara, Publication Date Unknown, retrieved Nov. 9, 2016 from http://www.unife.it/ing/lm.meccanica/insegnamenti/meccanica-delle-vibrazioni/materiale-didattico/copy_of_a-a-2016-17-dispense-e-programma/03-rao_cap1-fundamentals-of-vibration.pdf, 76 pages.

(Continued)

*Primary Examiner* — Ojiako K Nwugo
(74) *Attorney, Agent, or Firm* — Sheridan Ross PC

(57) ABSTRACT

Hand-washing systems and methods are proposed enabling monitoring, reminding, recording, and reporting functionalities. The hand-washing systems and methods include wearable devices equipped with RFID and vibration capabilities. The wearable RFID devices permit users to provide data pertaining to the hand-washing activities of the user in, for example, health care related settings. The data can be collected and, in turn, shared with relevant entities for reporting purposes.

20 Claims, 8 Drawing Sheets

(56) References Cited

U.S. PATENT DOCUMENTS

| | | | | |
|---|---|---|---|---|
| 2009/0195385 | A1* | 8/2009 | Huang | G08B 21/245 |
| | | | | 340/572.1 |
| 2010/0153374 | A1* | 6/2010 | LeBlond | G06Q 10/06398 |
| | | | | 707/722 |
| 2010/0265059 | A1* | 10/2010 | Melker | G08B 21/245 |
| | | | | 340/539.11 |
| 2010/0328076 | A1* | 12/2010 | Kyle | G06F 19/3418 |
| | | | | 340/573.1 |
| 2010/0328443 | A1* | 12/2010 | Lynam | G06K 9/00771 |
| | | | | 348/77 |
| 2011/0316703 | A1* | 12/2011 | Butler | G08B 21/245 |
| | | | | 340/573.1 |
| 2012/0112906 | A1* | 5/2012 | Borke | G16H 40/20 |
| | | | | 340/539.13 |
| 2012/0310664 | A1* | 12/2012 | Long | G06Q 10/06 |
| | | | | 705/3 |
| 2013/0127620 | A1* | 5/2013 | Siebers | G08B 21/02 |
| | | | | 340/573.1 |
| 2013/0187779 | A1* | 7/2013 | Pokrajac | G08B 21/245 |
| | | | | 340/573.1 |
| 2014/0266692 | A1* | 9/2014 | Freedman | G08B 21/245 |
| | | | | 340/539.11 |
| 2014/0297371 | A1* | 10/2014 | Colburn | G07C 1/10 |
| | | | | 705/7.38 |
| 2015/0221208 | A1* | 8/2015 | Knighton | G08B 21/245 |
| | | | | 340/573.1 |
| 2016/0125723 | A1* | 5/2016 | Marra | G08B 21/245 |
| | | | | 340/573.1 |
| 2016/0275779 | A1* | 9/2016 | Hajdenberg | G08B 21/245 |
| 2016/0371960 | A1* | 12/2016 | Haaland | G08B 21/245 |
| 2017/0229002 | A1* | 8/2017 | Wegelin | G08B 21/245 |
| 2017/0229003 | A1* | 8/2017 | Borke | G16H 40/20 |
| 2017/0256155 | A1* | 9/2017 | Sengstaken, Jr. | G06F 19/00 |
| 2018/0122214 | A1* | 5/2018 | Freedman | G08B 21/245 |

OTHER PUBLICATIONS

"PDC RFID Wristbands," PDC, Publication Date Unknown, retrieved Nov. 9, 2016 from http://waterparkrfid.com, 2 pages.

"Vibration Motors," Precision Microdrives, Publication Date Unknown, retrieved Nov. 9, 2016 from https://www.precisionmicrodrives.com/vibration-motors, 2 pages.

Doebbeling et al., "Removal of Nosocomial Pathogens from the Contaminated Glove: Implications for Glove Reuse and Hand Washing," Annals of Internal Medicine, 1998, vol. 109, No. 5, pp. 394-398, abstract only.

Ducel et al., Prevention of hospital-acquired infections: A Practice Guide, 2nd Ed., World Health Organization, 2002, retrieved from http://www.who.int/csr/resources/publications/drugresist/en/whocdscsreph200212.pdf, 72 pages.

Haley, "Measuring the costs of nosocomial infections: methods for estimating economic burden on the hospital," American Journal of Medicine, 1991, vol. 91, No. 3, pp. S32-S38, abstract only.

Pittet et al., "Bacterial Contamination of the Hands of Hospital Staff During Routine Patient Care," Archives of Internal Medicine, 1999, vol. 159, pp. 821-826.

Widmer et al., "Outbreak of Pseudomonas aeruginosa infections in a surgical intensive care unit: probable transmission via hands of a health care worker," Clinical Infectious Diseases, 1993, vol. 16, No. 3, pp. 372-376.

* cited by examiner

| DeviceID | SensorID | Timestamp |
|---|---|---|
| DrA | Patient0Door | 02:02:2015:1247 |
| DrA | Patient0Sink | 02:02:2015:1248 |
| DrA | Patient0Bed | 02:02:2015:1249 |
| DrA | Patient0Door | 02:02:2015:1250 |
| DrA | HallASink | 02:02:2015:1251 |
| DrA | Patent1Door | 02:03:2015:0752 |
| DrA | Patient1Door | 02:03:2015:0753 |
| DrA | Patient2Door | 02:03:2015:0754 |
| DrA | Patient2Bed | 02:03:2015:0755 |
| DrA | Patient2Door | 02:03:2015:0756 |
| DrA | HallASink | 02:03:2015:0757 |

*Fig. 3*

| DeviceID | SensorID | Timestamp | ... |
|---|---|---|---|

*Fig. 4A*

| DeviceID | Room | TYPE | Time | ... |
|---|---|---|---|---|

*Fig. 4B*

| DeviceID | Timestamp |
|---|---|
| DrA | 02:02:2015:1247 |
| DrA | 02:02:2015:1248 |
| DrA | 02:02:2015:1249 |
| DrA | 02:02:2015:1250 |
| DrA | 02:02:2015:1251 |
| DrA | 02:03:2015:0752 |
| DrA | 02:03:2015:0753 |
| DrA | 02:03:2015:0754 |
| DrA | 02:03:2015:0755 |
| DrA | 02:03:2015:0756 |
| DrA | 02:03:2015:0757 |

*Fig. 7A*

| USER | SENSOR | BED1 | BED2 | BED3 |
|---|---|---|---|---|
| DrA | DOOR | R | R | R |
| DrA | SINK | G | G | G |
| DrA | BED1 | G | R | R |
| DrA | SINK | G | G | G |
| DrA | DOOR | OFF | OFF | OFF |
| DrB | DOOR | R | R | R |
| DrB | SINK | G | G | G |
| DrB | BED2 | R | G | R |
| DrB | SINK | G | G | G |
| DrB | BED3 | R | R | G |
| DrB | SINK | G | G | G |
| DrB | DOOR | OFF | OFF | OFF |
| DrG | DOOR | R | R | R |
| DrG | SINK | G | G | G |
| DrG | BED1 | G | R | R |
| DrG | BED2 | R | R | R |
| DrG | SINK | G | G | G |

*7B*

SYSTEMS AND METHODS FOR HAND SANITIZATION MONITORING AND COMPLIANCE

This U.S. Non-Provisional Patent Application claims the benefit of priority from U.S. Provisional Application No. 62/452,851, filed Jan. 31, 2017, the entire disclosure of which is hereby incorporated by reference.

FIELD

The present disclosure is generally directed toward systems and methods used to monitor hand-sanitization practices of employees, and particularly directed toward monitoring the hand-sanitization practices of health-care providers and recording and reporting data to meet compliance requirements.

BACKGROUND

The medical advantages of hand washing can be traced as far back as 1847 stemming from the work of Semmelweis, who was an early pioneer in the field of aseptic procedures. Semmelweis instituted hand washing with non-medicated soap in combination with chlorinated lime solution and discovered decreases in mortality rates in patents. What Semmelwis's work uncovered, and the modern medical profession knows well today, is that microorganisms can be transferred from health care workers (HCWs) to patients and vice versa.

Most commonly, this transmission occurs is through direct contact by the HCW with the pathogen. The hands of HCWs may be colonized or contaminated with pathogens, such as *Staphylococcus aureus, Klebsiella pneumoniae, Acinetobacter* species, *Enterobacter* species, or *Candida* species, for example. In addition, it has been demonstrated that microorganisms accumulate on HCWs' hands over time during patient care. Therefore, hands of HCWs can transmit pathogens even without previous contact with other patients. Even using gloves does not completely protect against contamination of the hands.

Hospital acquired infections (HAIs), also known as nosocomial infections, are a serious public health problem and a major cause of morbidity and mortality. HAIs can also prolong the length of hospital stays thereby increasing costs throughout a healthcare system and further increase chances for additional infections. This problem of HAI is, in part, directly related to lack of compliance for hand washing amongst HCWs. The financial impact to hospitals, specifically, and the health care system, generally, is appreciable and unacceptable. HAIs stemming from failure to comply with hand-washing protocols is avoidable. Furthermore, strategies investing in systems and methods to minimize the occurrence of HAIs could potentially free up monies to be invested elsewhere, for instance, in renovations of the hospital, research and development, and recruitment and retention of HCWs.

SUMMARY

A long-felt and unmet need exists for systems and methods to monitor and record hand-sanitization practices of employees, and particularly monitoring and recording the hand-sanitization practices of WCWs. It is further advantageous for such recording and reporting of hand-washing methods to be compiled in useable data, which can be reported to show compliance with sanitary requirements.

The present disclosure is directed to a spatially activated reminding device to track users and their activities in a space. Furthermore, the present disclosure includes systems and methods that utilize modern technology in a novel way to meet hand-washing compliance requirements for HCWs: radio frequency identification (RFID) technology, vibration motors, and communication networks.

RFID is a generic term for technologies using radio waves to automatically identify people or objects. There are several methods of identification, but the most common is to store a serial number that identifies a person or object, and perhaps other information, on a microchip that is attached to an antenna (the chip and the antenna together are called an RFID transponder or an RFID tag). The antenna enables the chip to transmit the identification information to a reader. The reader converts the radio waves reflected back from the RFID tag into digital information that can then be passed on to computers that can make use of it.

An RFID system consists of a tag, which is made up of a microchip with an antenna, and an interrogator or reader with an antenna. The reader sends out electromagnetic waves. The tag antenna is tuned to receive these waves. A passive RFID tag draws power from field created by the reader and uses it to power the microchip's circuits. The chip then modulates the waves that the tag sends back to the reader and the reader converts the new waves into digital data.

Active RFID tags have a battery, which is used to run the microchip's circuitry and to broadcast a signal to a reader (the way a cell phone transmits signals to a base station). Passive tags have no battery. Instead, they draw power from the reader, which sends out electromagnetic waves that induce a current in the tag's antenna. Semi-passive tags use a battery to run the chip's circuitry, but communicate by drawing power from the reader. Active and semi-passive tags are useful for tracking high-value goods that need to be scanned over long ranges, such as railway cars on a track, but they cost a dollar or more, making them too expensive to put on low-cost items. Companies are focusing on passive UHF tags, which cost less than 50 cents today in volumes of 1 million tags or more. Their read range isn't as far—typically less than 20 feet vs. 100 feet or more for active tags—but they are far less expensive than active tags and can be disposed of with the product packaging.

Passive and active RFID transponders or tags contain coiled antennas to enable them to receive and respond to radio-frequency queries from an RFID reader or transceiver (which also includes an antenna). The transceiver converts the radio waves returned from the RFID tag into a form that can be passed onto computers. Typically, a serial number that identifies a product uniquely, and sometimes other information, is stored on the RFID tag (which typically can store up to 2 KB of data). Passive RFID tags do not have a power supply. A minute electrical current induced in an antenna by the incoming radio-frequency scan provides enough power for the tag to send a response. Active RFID tags have an on-board power source and may have longer ranges and larger memories than passive tags and the ability to store additional information sent by the transceiver. Semi-passive RFID tags use an on-board power source to run the tag's circuitry but communicate by drawing power from the transceiver. Chips in RFID tags can be read-write or read-only.

In embodiments a spatially activated reminding device utilizing RFID technology and vibration mechanisms remind the HCW to wash his or her hands upon entering and exiting the patient hospital room. When the HCW enters the room, a vibration may be activated on the wearable RFID device reminding the HCW to sanitize their hands utilizing known methods, including, without limitation, antiseptic gels, soaps, and foams, before and after making patient contact. The tactile stimulation being used may be randomized and pulse modulation employed each time provider enters and exits room, thus eliminating the chances of becoming immune to the reminder. The device may be paired with an RFID reading sensor which may be installed on a single or multiple locations; including: (1) door frames to patient rooms, (2) sink/hand gel sanitizing units throughout the hospital. In an embodiment, every sink or hand gel unit with a soap and/or hand-gel dispenser will be paired with a sensor and communication device. Every time the sink or hand gel unit is activated by dispensing soap and/or hand-gel, the sink or hand gel dispenser will send data corresponding to the activation to an appropriate data collection and analysis location. Data will then be collected from the sink and gel station activations and analyzed as a percentage compliance rate. This data will be compared to pre-existing HAI rates to determine the effectiveness of the product. Data will be utilized as a means to report percentage compliance rates which will then be used to communicate with billing insurance companies such as Medicare/Medicaid to negotiate new pricing for services provided given that they stay above a set percentage compliance rate.

Personal Wearable RFID Device

In an exemplary embodiment, a healthcare worker (HCW) wears or otherwise carries a personal device. The device may utilize one or more communication modules, for example a radio frequency identification (RFID) unit. The device may be in the form of or attached to a wearable article, for example a cellular telephone, bracelet, anklet, or necklace, or may be clipped onto clothing.

In some embodiments, the wearable device may comprise an RFID tag (comprising a microchip with an antenna) and a battery. The RFID tag may optionally be passive such that a battery would not be required, or active or semi-passive, in which a battery may be required. In addition to an RFID tag, the wearable device may comprise an RFID scanner. The wearable device may also comprise a processor in communication with memory and a storage device.

The wearable device may additionally comprise one or more feedback modules, including for example a speaker, a vibrator, and a display. The wearable device may comprise a speaker operable to perform one or more of a number of functions, e.g. beep upon low battery, beep upon crossing through a doorway, beep upon satisfying a requirement (e.g. visiting a handwashing station), sending a message to the wearer, etc.

The wearable device may comprise a vibrator module. The vibration module may comprise a motor in connection to a power source. The vibration module may be configured to cause a portion of the wearable device to vibrate at particular times. The vibration module may vibrate every time the wearable device is scanned by an RFID scanner, or scanned by a particular RFID scanner or a group of scanners. For example, a user wearing the wearable device may be notified via a vibration upon entering a patient room due to the wearable device being scanned by an RFID scanner on a doorframe.

The wearable device may comprise an LED light, or other form of display, may be used to track a battery level, flash upon crossing through a doorway, or flash upon satisfying some requirement (e.g. visiting a handwashing station).

The wearable device may comprise a communication module, for example one or more of a wireless network adapter, Bluetooth, USB, etc. In some embodiments, the wearable device comprises one or more communication modules. A communication module may comprise one or more of a wireless internet connection (Wi-Fi) adapter, Bluetooth, a USB connection, etc. The wearable device may be powered by a battery. Alternatively, in an embodiment the wearable device may be simply comprise an RFID tag with no power source.

The wearable device may comprise software operable to perform a number of functions. For example, in some embodiments, the wearable device may comprise an RFID scanner. Upon scanning a doorway RFID tag, the wearable device may be operable to perform a number of reactions in response. For example, the wearable device may vibrate in some pattern to remind the HCW to wash his or her hands. Alternatively, or in addition to vibrating, the wearable device may flash LED lights or make a noise upon scanning a doorway RFID tag. Tags in other locations or on particular doorways could be associated with different reactions.

In other embodiments, the wearable device may comprise an RFID tag which, when scanned by an RFID scanner, reacts in a number of possible ways. For example, an RFID scanner on a doorway may scan the wearable device upon the wearer crossing through the doorway. The wearable device may react by vibrating, lighting up, beeping, or some other way of notifying the user.

Scanners or RFID tags in other locations may be associated with different reactions. For example, different vibration patterns, beep tones, lights, etc. may be programmed based on a particular door, a particular sink/gel station, or a particular bedframe.

Bedframe RFID Scanners and/or Tags

RFID scanners and/or RFID tags may be affixed to stationary objects, such as doorframes, sink/gel stations, and beds.

In some embodiments, RFID scanners, or RFID readers, may be positioned on doorframes and operable to scan wearable devices as an HCW wearing a wearable device walks through the door. Such an RFID scanner may be operable to alert the wearable device it has been scanned, as well as record into a storage device connected to the RFID scanner a database entry listing a wearable device ID and a timestamp in association with the scanned wearable device.

In embodiments wherein a doorframe is equipped with an RFID scanner, the scanner may be in communication with a number of elements, for example a memory and storage device, a processor, a battery or other electrical power component, an LED or other display device, a speaker, and/or a network connection (e.g. a Wi-Fi adapter, Ethernet cable, or other device). In such embodiments, the RFID scanner should be operable to record instances of wearable devices being read by the scanner. A database may be created and stored in memory or other storage on the scanner device. The database may otherwise be stored on a server connected to one or more RFID scanners via a network connection. Database entries may comprise instances of scanned HCW wearable devices.

In an exemplary embodiment, a database may be created and stored on an RFID doorframe scanner device hard drive, the database storing instances of HCW wearable devices scanned by said particular doorframe scanner device. Such a database, or entries thereof, may be transmitted via a network and combined with databases from other scanners to create a master database comprising a list of all wearable devices scanned by all readers throughout the network.

In some embodiments, doorframes may be equipped with passive RFID tags. In such embodiments, a wearable device worn by a HCW may be operable to scan such tags and record each instance of scanning.

Sink and Gel Station RFID Sensors, Scanners, Readers, and Tags

In some embodiments, RFID scanners, or RFID readers, may be positioned on or around a sink and/or gel station and operable to scan wearable devices as an HCW wearing a wearable device approaches and/or uses the sink and/or gel station. Such an RFID scanner may be operable to alert the wearable device it is being scanned, as well as record into a storage device connected to the RFID scanner a database entry listing a wearable device ID and a timestamp in association with the scanned wearable device.

In embodiments wherein a sink and/or gel station is equipped with an RFID scanner, the scanner may be in communication with a number of elements, for example a memory and storage device, a processor, a battery or other electrical power component, an LED or other display device, a speaker, and/or a network connection (e.g. a Wi-Fi adapter, Ethernet cable, or other device). In such embodiments, the RFID scanner should be operable to record instances of wearable devices being read by the scanner. A database may be created and stored in memory or other storage on the scanner device. The database may otherwise be stored on a server connected to one or more RFID scanners via a network connection. Database entries may comprise instances of scanned HCW wearable devices.

In an exemplary embodiment, a database may be created and stored on an RFID sink and/or gel station scanner device hard drive, the database storing instances of HCW wearable devices scanned by said particular sink and/or gel station scanner device. Such a database, or entries thereof, may be transmitted via a network and combined with databases from other scanners to create a master database comprising a list of all wearable devices scanned by all readers throughout the network. In some embodiments, sinks and/or gel stations may be equipped with passive RFID tags. In such embodiments, a wearable device worn by a HCW may be operable to scan such tags and record each instance of scanning.

In certain embodiments, a sink and/or hand gel unit can be equipped with an automatic soap and/or hand-gel dispenser. Upon activation of the automatic soap and/or hand-gel dispenser by a user to disinfect the HCW's hands, a signal will be communicated from the sink and/or hand gel unit though one or more paired sensors and/or communication devices. Every time the sink and/or hand gel unit is activated by the HCW to dispense soap and/or hand-gel, the sink and/or hand gel dispenser will send data corresponding to the activation to an appropriate data collection and analysis location. The sink can be programmed to only send data when soap and/or gel is either automatically dispensed or manually dispensed, and not send data upon dispensing only water.

Bedframe RFID Scanners, Readers, and/or Tags

In some embodiments, RFID scanners, or RFID readers, may be positioned on bedframes and operable to scan wearable devices as an HCW wearing a wearable device walks near or up to a bed. Such an RFID scanner may be operable to alert the wearable device it has been scanned, as well as record into a storage device connected to the RFID scanner a database entry listing a wearable device ID and a timestamp in association with the scanned wearable device.

In embodiments wherein a bedframe is equipped with an RFID scanner, the scanner may be in communication with a number of elements, for example a memory and storage device, a processor, a battery or other electrical power component, an LED or other display device, a speaker, and/or a network connection (e.g. a Wi-Fi adapter, Ethernet cable, or other device). In such embodiments, the RFID scanner should be operable to record instances of wearable devices being read by the scanner. A database may be created and stored in memory or other storage on the scanner device. The database may otherwise be stored on a server connected to one or more RFID scanners via a network connection. Database entries may comprise instances of scanned HCW wearable devices.

In an exemplary embodiment, a database may be created and stored on an RFID doorframe scanner device hard drive, the database storing instances of HCW wearable devices scanned by said particular bedframe scanner device. Such a database, or entries thereof, may be transmitted via a network and combined with databases from other scanners to create a master database comprising a list of all wearable devices scanned by all readers throughout the network. In some embodiments, bedframes may be equipped with passive RFID tags. In such embodiments, a wearable device worn by a HCW may be operable to scan such tags and record each instance of scanning.

In yet another embodiment, a room could have multiple beds and the system could notify a HCW to wash his/her hands after the HCW's wearable device has been scanned by a bedframe RFID scanner.

LED "Bed Guard", "Stop/Go" Feature

In one embodiment, a hospital room may be equipped with an LED "bed guard" or "stop/go" feature. This feature may be particularly useful in contact isolation cases. In such an embodiment, a bed in a hospital room may be surrounded by lights placed in the floor. The lights may operate to alert HCW of a requirement to perform some function upon entering the room. For example, the lights may turn red upon detecting a HCW entering the room. The lights may remain red until (1) the HCW visits the sink and/or gel station to wash his/her hands, or (2) the HCW exits the room, at which point the lights may turn off or turn green or otherwise alert the HCW of the possibility of approaching the bed.

In some embodiments, the lights are to remain red at all times except when a HCW is detected entering a room and then his/her wearable device is scanned by a sink or gel station RFID scanner. In other embodiments, the lights are to remain off at all times except when a HCW is detected entering a room, at which point the lights turn red. If the HCW is detected as approaching the sink/gel station, the lights may turn green. If the HCW is detected as leaving the room, the lights may turn off.

In yet another embodiment, the lights may turn back to red upon detecting a second HCW entering the room, despite having turned green for a first HCW after the first HCW is detected as using the sink/gel station.

In embodiments wherein a room is equipped with a "Bed Guard" function, the LED lights may be in communication with a number of elements, for example a memory and storage device, a processor, a battery or other electrical power component, a display device, a speaker, and/or a network connection (e.g. a Wi-Fi adapter, Ethernet cable, or other device). In such embodiments, the "Bed Guard" function should be operable to record instances of the "Bed Guard" function being used. A database may be created and stored in memory or other storage on the scanner device. The database may otherwise be stored on a server connected to one or more RFID scanners via a network connection. Database entries may comprise instances of scanned HCW wearable devices.

A bed guard function processor may operate in communication with doorframe, bedframe, and sink/gel station RFID scanners within the room and compile a database of all instances such scanners read wearable device RFID tags. Such a database may be used to verify the functionality of the bed guard function, the obedience of HCW to follow guidelines, and for the processor to determine in which state the LED lights should be.

In yet another embodiment, a room could have multiple beds and a number of bed guard function systems could be used to control the movement of doctors and nurses throughout a hospital room, and could notify a HCW to wash his/her hands after the HCW's wearable device has been scanned by a bedframe RFID scanner. For example, if a doctor enters a room with three beds, the bed guard functions of all three beds could turn red. After doctor visits a sink, all three could turn green. After doctor visits the first bed, the other two beds could turn red. After the doctor returns to the sink, all three beds could return to green. After the doctor is scanned exiting the room, all three bed guard functions could turn off.

Another embodiment of the bed guard function could operate with a display monitor as opposed to or in addition to LED lights. For example, if three doctors, A, B, and G, are scanned entering a hospital room with one bed, a monitor could display the names of detected wearable devices. The names could appear red to signify the doctors have not yet visited the sink/gel station. After doctor A visits the gel station, his name could turn green, signifying permission to visit the bed. This system could be expanded for a room with multiple beds, wherein each bed has a separate monitor, or a large monitor could show statuses of all HCWs with wearable devices in the room for each bed.

Servers/Databases

All sensors within a hospital may be operably connected to a computer or server located in the hospital or externally. Information collected from the sensors may be sent to third parties, e.g. insurance companies. For example, an insurance company may use sensor data to verify the completion of proper procedure within a hospital to provide benefits to cooperating hospitals or to adjust rates based on good hospital behavior.

In embodiments, sensor data is sent to a server from a sensor via packets comprising database entries for each instance of the sensor reading a wearable device. For example, a doorframe mounted sensor may operate to be directly connected via a network to a server and send each scanner reading, comprising, e.g., a wearable device ID, a timestamp, and a sensor ID. Each sensor may be assigned a sensor ID so that the sensors may easily be identified and associated with other sensors in the same or nearby rooms. For example, room 321 may comprise sensors with sensor IDs of Door321, Sink321, and BedFrame321. Similarly, wearable devices may be associated with wearable device IDs so that wearers of each device may be identified. For example, a Doctor Alex may wear a wearable device with a wearable device ID of DrA. When Dr. Alex walks into room 321, the doorframe RFID sensor should read his wearable device ID and send a database entry to the server identifying the sensor as Door321 and the wearable device as DrA.

The data collected from the sensors may be monitored over time and used to compare a hospital to other hospitals or compare wards or floors within a hospital. The sensor data may also be used to conduct other research, for example percentage compliance rates, to keep track of who was in what room at what time, and to keep track of where people are at the present time in order to be better able to track people down and page people.

The system disclosed herein may be used in any number of combinations of the features described. For example, a beginner option could be used by a hospital to simply remind HCWs entering a room to perform a function. Such a system could be implemented simply via a wearable device and a door mounted RFID scanner. An intermediate option could be used wherein HCWs wear wearable devices, and data is collected from RFID scanners on doorframes and/or sink/gel stations. An advanced option could be used with all or some of the functions described herein.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the embodiments.

FIG. 3 is a block diagram depicting details of a database hierarchical structure in accordance with embodiments of the present disclosure.

FIGS. 4A and 4B are block diagrams depicting details of exemplary packets in accordance with embodiments of the present disclosure.

FIGS. 7A and 7B are block diagrams depicting details of an additional database hierarchical structure in accordance with embodiments of the present disclosure.

DETAILED DESCRIPTION

Figure 1:
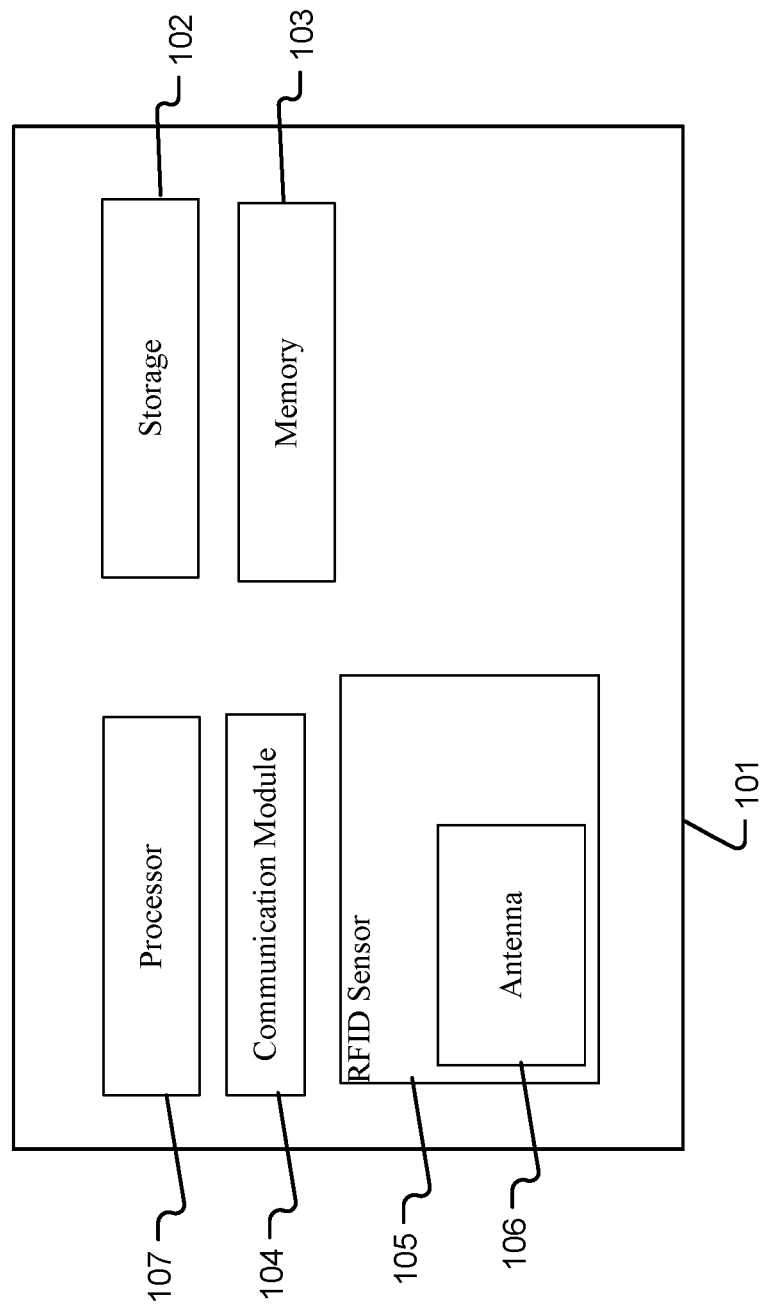
FIG. 1 is a block diagram depicting details of an RFID scanner device in accordance with embodiments of the present disclosure.

FIG. 1 illustrates an exemplary RFID scanner device 101. Such a scanner device 101 may be installed on a doorframe, sink/gel station, bedframe, or any location to operate to scan a wearable device as discussed herein or any RFID tag. As illustrated in FIG. 1, a scanner may comprise a processor 107, a storage device 102, a memory device 103, a communication module 104, an RFID sensor 105, and an antenna 106. An RFID scanner to be used in the system disclosed herein may comprise any or all of the features illustrated in FIG. 1.

Figure 2:
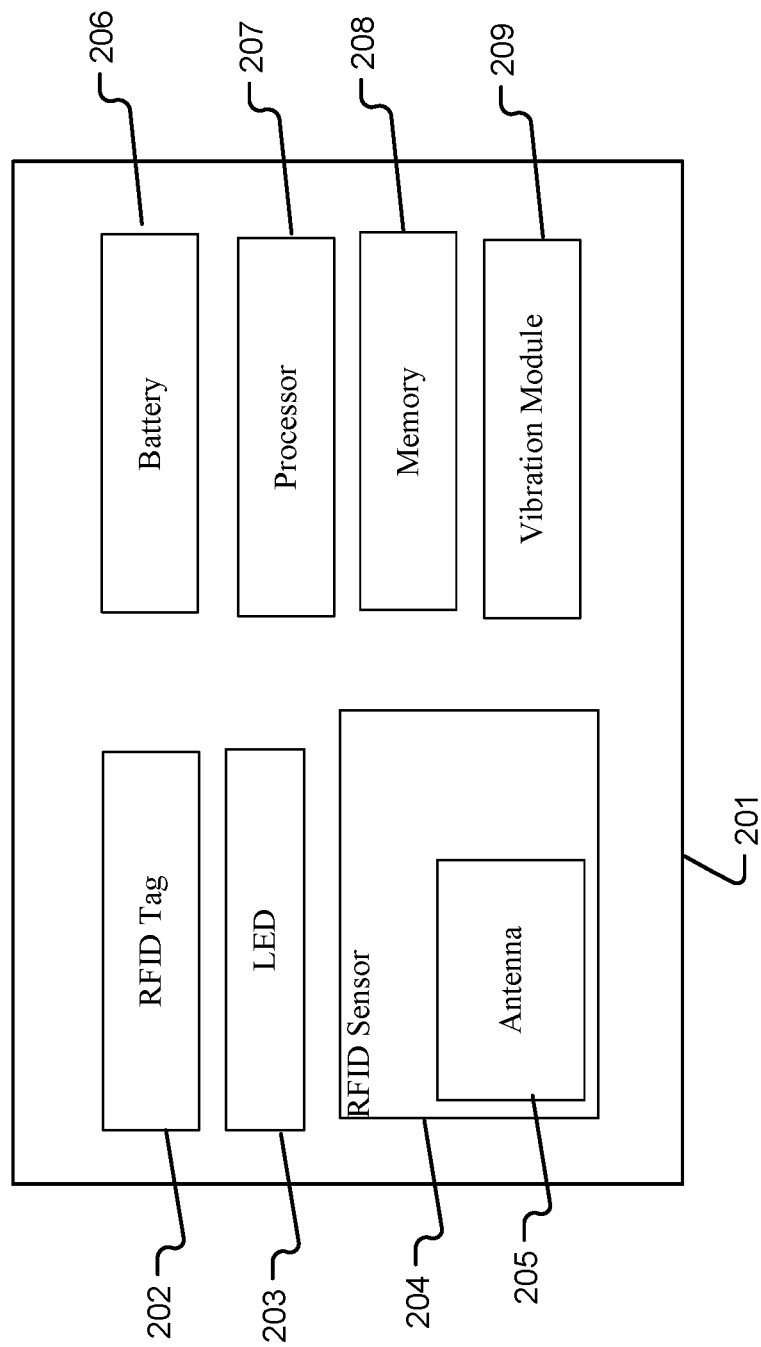
FIG. 2 is a block diagram depicting details of a wearable device in accordance with embodiments of the present disclosure.

FIG. 2 illustrates an exemplary wearable device 201. Such a wearable device 201 may comprise an RFID tag 202 or an RFID scanner 204 with an antenna 205, or a combination thereof. The wearable device 201 may also comprise one or more of an LED light 203, a battery 206, a processor 207, a memory device 208, and a vibration module 209. A wearable device to be used in the system disclosed herein may comprise any or all of the features illustrated in FIG. 2.

The vibration module 209 may comprise various types of vibration motors. For example, the vibration module 209 may include an eccentric rotating mass vibration motor (ERM), which utilizes a small unbalanced mass on a DC motor. When the ERM rotates it creates a force that translates to vibrations. Further, a linear resonant actuator (LRA) contains a small internal mass attached to a spring, which creates a force when driven. The present disclosure contemplates two aspects of vibration: vibration frequency, and vibration amplitude. Vibration frequency is denoted in hertz which is measured as Hz=1 cycle per second. Thus, vibration frequency (Hz) is RPM/60.

Vibration amplitude is the strength of the force generated by the motor which can be determined by the following equation: $F=(m)(r)(w^2)$. F=centripetal force in Newtons (N). m=Mass of eccentric mass in (Kg). r=Eccentricity of eccentric mass (m). w=Angular velocity (Rads−1) aka Radians per second. The wearable device 209 as contemplated herein may, thus, be designed to emit vibrations at various frequencies and amplitudes.

FIG. 3 illustrates an exemplary database 300 storing information collected by a number of sensors as described herein. The database 300 may comprise a number of database entries (304, 305, 306) comprising a DeviceID 301, a SensorID 302, and a Timestamp 303. For example, a sensor with the SensorID 302 of "Patient0Door" may scan a wearable device with a DeviceID of "DrA" on Feb. 2, 2015 at 12:47 PM. A database entry 304 may be created storing this information and stored on a server connected via a network to the Patient0Door sensor. This information may be collected to conduct analysis, for example, in the database 300 illustrated in FIG. 3, it can be seen that DrA, after entering Patent0Door, visited the sink station before approaching the bed. In contrast, it can be seen that DrA entered Patient2Door and approached Patient2Bed without being scanned by a sink/gel station RFID scanner.

FIG. 4A illustrates an exemplary packet 410 sent from a sensor to a server database via a network. The packet 410 may comprise fields for factors such as a device ID 411, a sensor ID 412, and a timestamp 413. Other fields 414 may be used for any other information needed for a database, such as a room number, a hospital ID, a ward ID, etc.

FIG. 4B illustrates a second exemplary packet 420 sent from a sensor to a server database via a network. The packet 420 may comprise fields for factors such as a device ID 421, a sensor ID 422, a type 423 (e.g. Door, Sink, Bed) and a timestamp 424. Other fields 425 may be used for any other information needed for a database, such as a room number, a hospital ID, a ward ID, etc.

Figure 5:
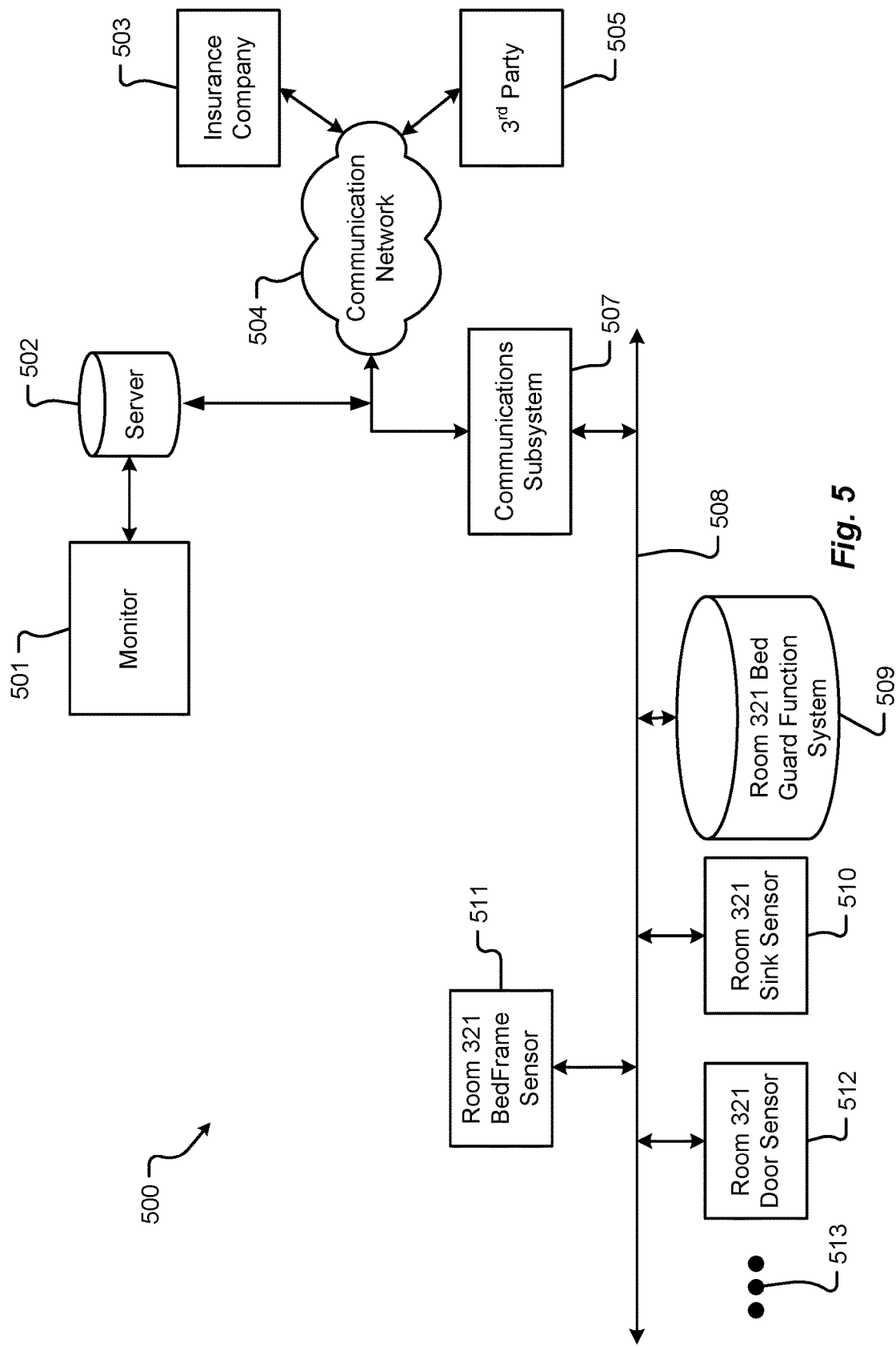
FIG. 5 is a block diagram depicting details of a communication system in accordance with embodiments of the present disclosure.

FIG. 5 illustrates an exemplary system 500 as described herein. The system 500 may comprise a server 502 with a monitor 501 connected to a communication network 504. The server 502 may be accessed by an insurance company 503 via the communication network 504 as well as by one or more third parties 505. The communication network may connect to the sensors via a communication sub system 507 and a network 508. The sensors of the system 500 may comprise a bedframe sensor 511, a bed guard function system 509, a sink/gel station sensor 510, a door sensor 512, and/or other sensors 513.

Figure 6A:
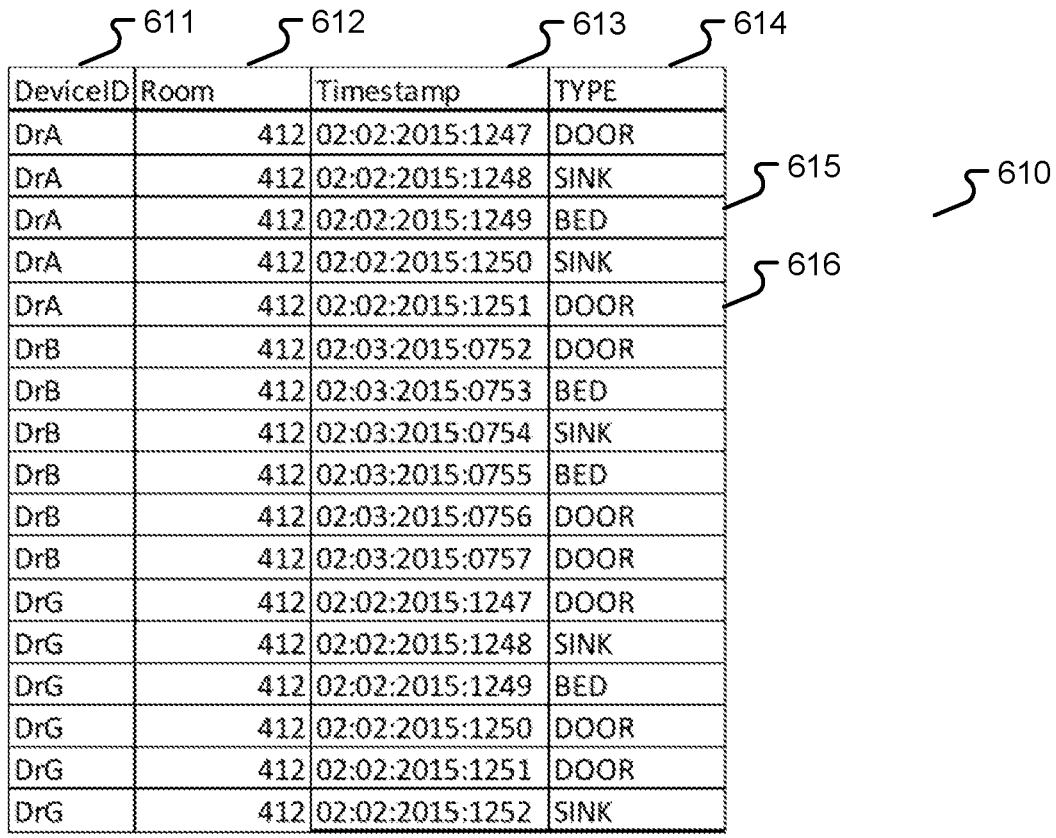
FIGS. 6A and 6B are block diagrams depicting details of an additional database hierarchical structure in accordance with embodiments of the present disclosure.

FIG. 6A illustrates an exemplary database 610 which may be stored on a server operably connected to a number of sensors. Such a database may comprise fields for a device ID 611, a Room number 612, a timestamp 613, and a sensor type 614. For example, a database entry 615 may show a device with a device ID of DrA was scanned by a BED sensor in room 412 at 12:49 on Feb. 2, 2015. A second DOOR scan, or a DOOR scan following a BED or SINK scan may show a doctor has left a room. Such a scan may be shown via an entry in the database, e.g. database entry 616.

Figure 6B:
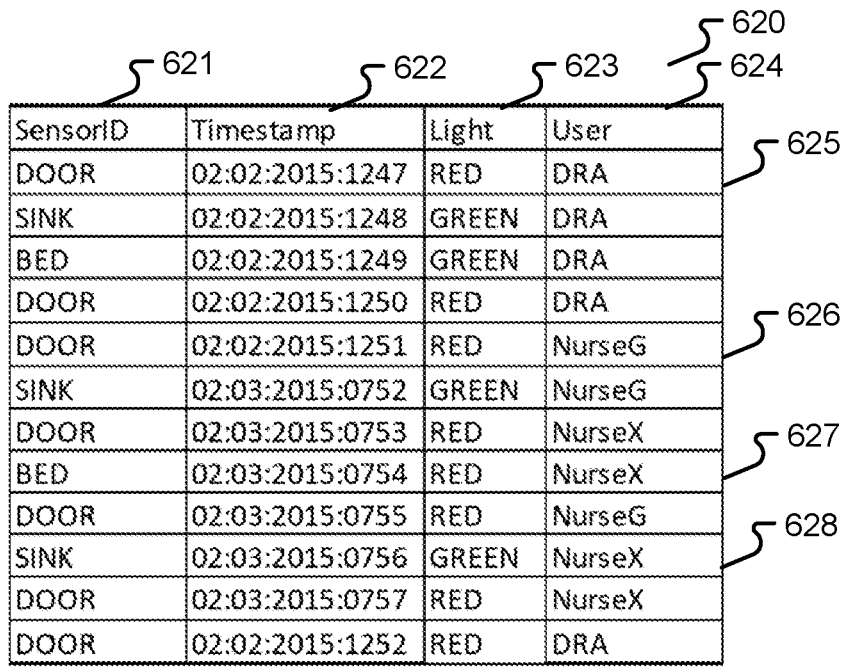

FIG. 6B illustrates an exemplary database 620 which may be stored on a server operably connected to a number of sensors and used to operate a "Bed Guard" function. Such a database may comprise fields for a sensor ID 621, a timestamp 622, a "Bed Guard" light status 623, and a user ID 624. For example, a database entry 625 may show a device with data showing that a DOOR sensor scanned a wearable device associated with a DRA. The lights of the "Bed Guard" system, upon detecting a user entering a door turn red as shown in the database entry 625. The light status may change, for example after the doctor enters the door and approaches the sink station, the lights may turn green. The database may show details for a number of wearable devices, such as NurseG in database entry 626, and NurseX in database entry 627. As seen in the database entry 628, NurseX visited the sink sensor and the bed guard function lights turned Green.

FIG. 7A illustrates an exemplary database 700 associated with a single sensor describing the scanned devices with the device ID data field as well as a timestamp in a timestamp field 702. Example entries 703, 704 and 705 show a wearable device with a device ID of DrA was scanned by the sensor a number of times.

FIG. 7B illustrates an exemplary database used to control the function of a bed guard function for a hospital room with a number of beds. In this example, a room with three beds has lights for each of the three beds. When a first user is scanned by a door sensor the lights for all three beds turn red. When the first user visits the sink, all three door lights turn green. When the first user visits a bed number 1, the bed number 1 lights remain green while the lights for the other beds may turn red. When the first user leaves the room, the lights may turn off. Such a database entry 716 shows userID 711 of DrA scanned by sensorID 712 of DOOR and the light status of Bed1 713, Bed2 714, and Bed3 715 as turn off. When a second user, as shown in entry 717, enters and visits the sink, all lights turn green. When the second user, as shown in entry 718, leaves the room, the lights may turn off.

Figure 8:
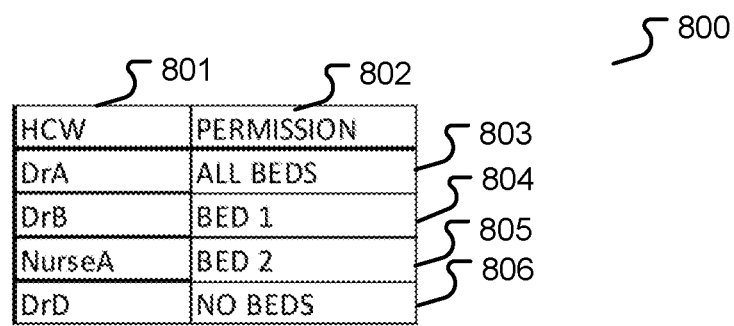
FIG. 8 is a block diagram depicting details of an exemplary display in accordance with embodiments of the present disclosure.

FIG. 8 illustrates an exemplary display for use in a hospital room computer monitor, showing permissions for a number of users. For example, if a DrA has entered a room and washed his hands, the monitor may show under a column HCW 801 that DrA has permission 802 to visit any and all beds (entry 803). DrB may have washed her hands and visited Bed1, thus the system shows DrB has permission to visit only Bed1 in entry 804. Nurse A may have similarly washed his hands and visited Bed 2 in entry 805, and DrD may have entered the room but has not yet washed her hands and thus is shown to have no permission to visit any beds. The display may be shown in sight of all in the room so that each user in the room may quickly assess the current permission status for themselves and other users. This monitor information may be communicated via a network to a master monitor in a control room for the hospital.

Figure 9:
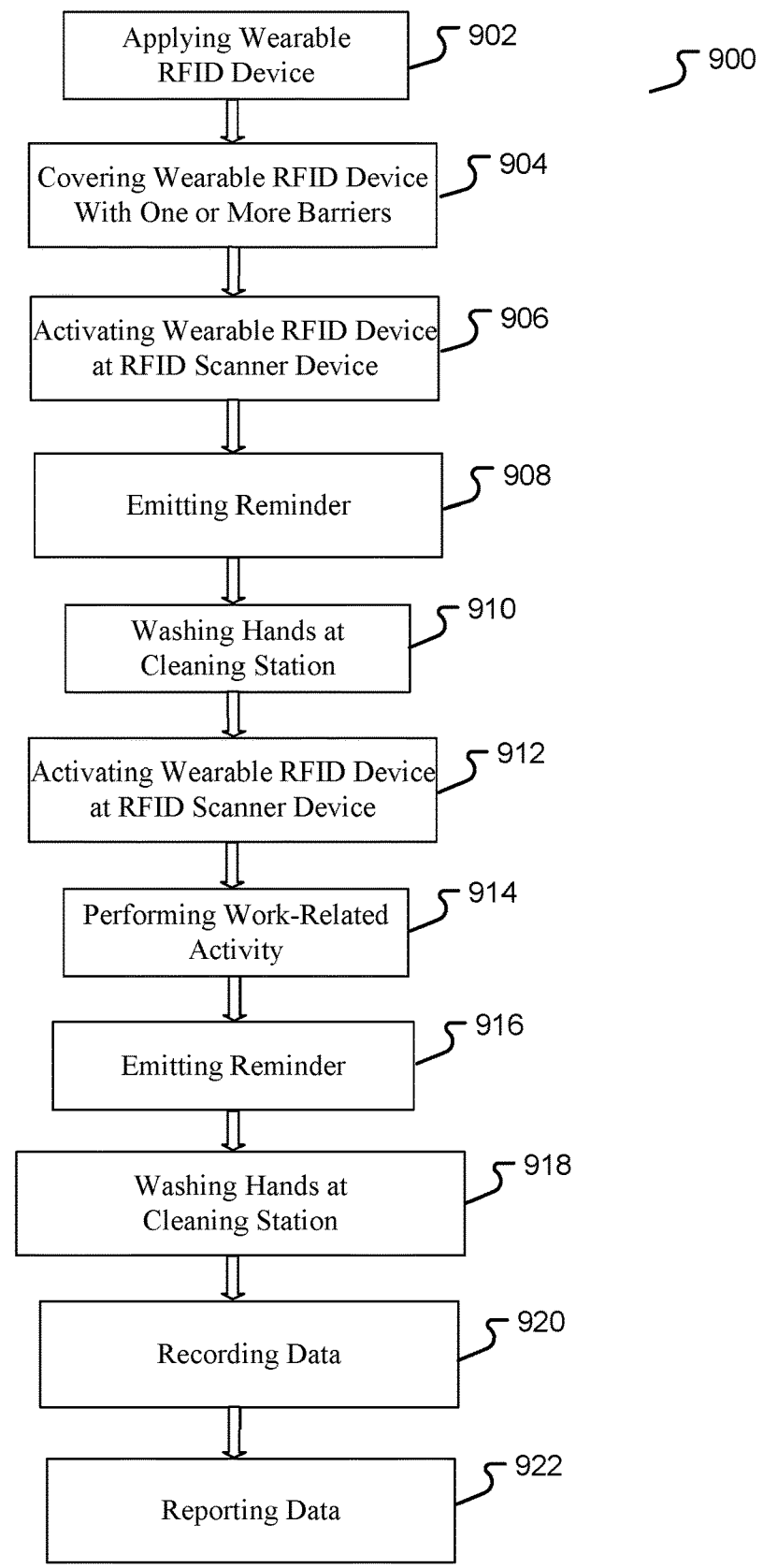
FIG. 9 is a flow diagram depicting a hand-washing monitoring method in accordance with embodiments of the present disclosure Drawings are not necessarily to be interpreted as being drawn to scale, or to any one particular scale.

FIG. 9 illustrates an exemplary method of employing a hand-washing system according to various embodiments of the present disclosure. The method is initiated when a user applies a wearable RFID device 201 (step 902). In embodiments the user optionally covers the wearable RFID device with one or more barriers step 904. Barriers may include garments of clothing. Such articles of clothing may include a cotton or wool sock or nylon stocking. Additional articles of clothing include pant legs, skirts, or scrubs.

Once the wearable RFID device 201 is applied to the user, the user may activate the wearable RFID device at a first RFID scanner device 101 (step 906). Optionally, a vibration module 209 reminds the HCW to wash his or her hands upon entering or exiting the patient hospital room (step 908). For example, when the HCW enters the room, a vibration, or other method of notification including audible sound or visible light, may be activated on the wearable RFID device reminding the HCW to sanitize their hands utilizing known methods, including, without limitation, antiseptic gels, soaps, and foams, before and after making patient contact (step 910).

In embodiments of the disclosure, the method includes the additional steps including activating the wearable RFID device 201 at an RFID scanner device 101 at or near the patients' location (step 912). As an additional and optional step (step 916), a vibration module 209 reminds the HCW to wash his or her hands after completion of performing the work-related activity (step 914). After the HCW washes his or her hands (steps 910 and 918), an RFID scanner device 101 located at the cleaning station 510 may record (step 920) and report (step 922) compliance data according to the embodiments of the present disclosure. Furthermore, any RFID scanner device 101 regardless of its location may function to record (step 920) and report (step 922) compliance data as contemplated in the present disclosure.

The phrases "at least one", "one or more", "or", and "and/or" are open-ended expressions that are both conjunctive and disjunctive in operation. For example, each of the expressions "at least one of A, B and C", "at least one of A, B, or C", "one or more of A, B, and C", "one or more of A, B, or C", "A, B, and/or C", and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any computer-readable storage and/or transmission medium that participate in providing instructions to a processor for execution. Such a computer-readable medium can be tangible, non-transitory, and non-transient and take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

A "computer readable storage medium" may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may be any computer readable medium that is not a computer readable storage medium and that can communicate, propagate, or transport a program for use by or in connection with an instruction execution system, apparatus, or device. A computer readable signal medium may convey a propagated data signal with computer readable program code embodied therein, for example, in baseband or as part of a carrier wave. Such a propagated signal may take any of a variety of forms, including, but not limited to, electro-magnetic, optical, or any suitable combination thereof. Program code embodied on a computer readable signal medium may be transmitted using any appropriate medium, including but not limited to wireless, wireline, optical fiber cable, RF, etc., or any suitable combination of the foregoing. The terms "determine", "calculate" and "compute," and variations thereof, as used herein, are used interchangeably and include any type of methodology, process, mathematical operation or technique.

The term "means" as used herein shall be given its broadest possible interpretation in accordance with 35 U.S.C., Section(s) 112(f) and/or 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

The term "module" as used herein refers to any known or later developed hardware, software, firmware, artificial intelligence, fuzzy logic, or combination of hardware and software that is capable of performing the functionality associated with that element.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented herein. As will be appreciated, other aspects, embodiments, and/or configurations of the disclosure are possible utilizing, alone or in combination, one or more of the features set forth above or described in detail below. Also, while the disclosure is presented in terms of exemplary embodiments, it should be appreciated that individual aspects of the disclosure can be separately claimed.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

I claim:

1. A wearable device, the device comprising:
    a power supply;
    a processor;
    a vibration module;
    a radio frequency identification-enabled (RFID) sensor;
        wherein the RFID sensor and the processor selectively receives electrical power from the power supply;
        wherein the processor is in communication with the vibration module and the RFID sensor;
    an antenna;
    a communication module;
    a memory operable to store at least one of data and instructions for execution by the processor;
        wherein the antenna and memory selectively receives electrical power from the power supply;
        wherein the antenna receives radio frequency signals for transmission as electrical signals to the RFID sensor;
        wherein the antenna further transmits radio frequency signals received as electrical signals from the processor;
        wherein the wearable device is operable to communicate with an RFID scanner device; and
        wherein the wearable device is further operable to communicate with a bed guard system, wherein the bed guard system employs at least one light emitting diode (LED) energized in response to a hand-sanitization requirement of one or more health care workers (HCWs) determined by the processor and signaled via the wearable device to the bed guard system.

2. The wearable device of claim 1, wherein the RFID scanner device comprises:
    a second processor;
    a communication module;
    a second RFID sensor;
    a second antenna; and
    a second memory.

3. The wearable device of claim 2, wherein the wearable device is in further operable to communicate, via the RFID scanner device with components of a network, the network comprising:
    at least one server;
    at least one monitor; and
    a plurality of RFID scanner devices.

4. The wearable device of claim 3, wherein at least one of the plurality of RFID scanner devices comprises at least one of a door sensor, a hand-washing station sensor, and a bed frame sensor.

5. The wearable device of claim 3, wherein the RFID scanner device, via the network, is operable to communication with one or more third parties.

6. The wearable device of claim 5 wherein data, comprising the hand sanitation requirement, is communicated, via the network, to the one or more third parties.

7. An electronic hand-washing reminder system, the system comprising:
   (a) one or more wearable devices, each of the one or more wearable devices comprising:
      (i) a vibration module;
      (ii) a radio frequency identification-enabled (RFID) sensor;
   (b) one or more RFID scanner devices, wherein the one or more RFID scanner devices is in communication with
      (a) the one or more wearable devices;
   (c) a bed guard function system, wherein the bed guard function system comprises:
      (i) a plurality of LED lights;
      (ii) a monitor display device;
      (iii) a memory storage device;
      (iv) a processor; and
      (v) a network connection, wherein the one or more wearable devices is in communication with the bed guard function system, and wherein the one or more wearable devices activates the plurality LED lights.

8. The electronic hand-washing reminder system of claim 7, wherein each of (b) the one or more RFID scanner devices comprises:
   (i) a processor;
   (ii) a communication module;
   (iii) an RFID sensor;
   (iv) an antenna;
   (v) a battery;
   (vi) storage; and
   (vii) memory.

9. The electronic hand-washing reminder system of claim 7, the system further comprising:
   a wherein each of (b) the one or more RFID scanner devices comprises:
      (i) a processor;
      (ii) a communication module;
      (iii) an RFID sensor;
      (iv) an antenna;
      (v) storage; and
      (vi) memory.

10. The electronic hand-washing reminder system of claim 7, wherein the (b) one or more RFID scanner devices is located at a bedframe.

11. The electronic hand-washing reminder system of claim 7, wherein the (b) one or more RFID scanner devices is located at a hand washing station.

12. The electronic hand-washing reminder system of claim 7, wherein the (b) one or more RFID scanner devices is located at a plurality of hand washing stations and a plurality of bedframes.

13. A method of reminding one or more health care workers to sanitize their hands, the method comprising:
   activating a wearable radio frequency identification-enabled (RFID) device;
   emitting a reminder to sanitize hands; and
   monitoring hand-sanitizing activities;
   activating a bed guard function system, wherein the bed guard function system is in communication with the wearable RFID device, and wherein the bed guard system employs a plurality of light emitting diodes (LEDs) to alert one or more health care workers (HCWs) of hand-sanitization requirements.

14. The method of claim 13, wherein the step of activating a wearable RFID device comprises:
   communicating between the wearable RFID device and an RFID scanner device.

15. The method of claim 14 further comprising:
   recording data associated with hand-sanitizing activities; and
   reporting data associated with hand-sanitizing activities.

16. The method of using an electronic hand-washing reminder system of claim 15, wherein the step of reporting data associated with hand-sanitizing activities consists of reporting data associated with hand-sanitizing activities to an insurance company.

17. The method of using an electronic hand-washing reminder system of claim 15, wherein the step of reporting data associated with hand-sanitizing activities consists of reporting data associated with hand-sanitizing activities to a United States federal health care agency.

18. The method of claim 15, wherein the step of reporting data associated with hand-sanitizing activities consists of reporting data associated with hand-sanitizing activities to a state health care agency.

19. The method of claim 14, wherein the RFID scanner device is located at the bed guard function system.

20. The method of claim 14, wherein the RFID scanner device is located at a hand sanitizing station.

\* \* \* \* \*